United States Patent [19]

Wagner

[11] Patent Number: 5,045,073

[45] Date of Patent: Sep. 3, 1991

[54] DIGITAL APPLICATOR AND PROGRAM

[76] Inventor: Eugene C. Wagner, 9 Tanglewild Pl., Chappaqua, N.Y. 10514

[21] Appl. No.: 500,588

[22] Filed: Mar. 28, 1990

[51] Int. Cl.$^5$ .................... A61M 35/00; A46B 5/04
[52] U.S. Cl. ........................................ 604/310; 401/7
[58] Field of Search ............................ 604/1–3, 604/289, 290, 292, 310; 606/162; 128/155, 844, 62 A; 433/216; 401/7, 8

[56] References Cited

U.S. PATENT DOCUMENTS

| | | | |
|---|---|---|---|
| 1,168,998 | 1/1916 | Brandenburg . | |
| 1,381,829 | 6/1921 | Hartman | 606/162 |
| 2,167,129 | 7/1939 | Sleeper . | |
| 2,396,548 | 3/1946 | Allen . | |
| 2,763,885 | 9/1956 | Lyons . | |
| 2,778,045 | 1/1957 | Bly et al. . | |
| 2,883,691 | 4/1959 | Gruenwald . | |
| 2,921,590 | 1/1960 | Holton . | |
| 3,018,484 | 1/1962 | Koehn | 128/844 |
| 3,409,010 | 11/1968 | Kron | 604/292 |
| 3,583,019 | 6/1971 | Conklin, Jr. . | |
| 3,798,698 | 3/1974 | Conklin, Jr. . | |
| 3,902,509 | 9/1975 | Tundermann et al. | 433/216 |
| 4,134,172 | 1/1979 | Arce . | |
| 4,162,553 | 7/1979 | Bruno . | |
| 4,335,731 | 6/1982 | Bora, Jr. | 433/216 |
| 4,665,901 | 5/1987 | Spector | 128/62 A |
| 4,701,168 | 10/1987 | Gammons | 604/310 |
| 4,902,283 | 2/1990 | Rojko | 604/292 |

FOREIGN PATENT DOCUMENTS

| | | | |
|---|---|---|---|
| 2055019 | 5/1972 | Fed. Rep. of Germany | 604/289 |
| 2099305 | 12/1982 | United Kingdom | 433/216 |
| 2130887 | 6/1984 | United Kingdom | 433/216 |

*Primary Examiner*—John D. Yasko
*Assistant Examiner*—Sharon Finkel
*Attorney, Agent, or Firm*—Natter & Natter

[57] ABSTRACT

A digital applicator for topically applied medicaments includes a dactyl cot formed of a tubular casing having a closed distal end. A conical dispenser formed of an absorbent material such as sponge is attached to the distal end. The casing wall is sufficiently thin and flexible so as not to significantly inhibit tactile sensitivity. Absorbed in the dispenser is a quantity of medicament with force exerted by the tip of a dactyl serving to compress the dispenser, thereby extruding a desired dosage of medicament on an affected area. The casing may be coiled in a toroid and sealed in a packet prior to use and the dispenser may be charged with medicament prior to packaging. Alternately, the user may absorb a desired quantity of medicament in the dispenser and then proceed with applying the medicament.

15 Claims, 1 Drawing Sheet

DIGITAL APPLICATOR AND PROGRAM

BACKGROUND OF THE INVENTION

1. Field of the Invention

This invention relates generally to applicators and more particularly to devices for improving the dactyl application of topical medicaments and other preparations.

2. Related Art

Numerous medicaments in cream, ointment and liquid bases have been formulated for topical application. In many instances, the preparations have been applied with a bare dactyl. This approach was both unsanitary and inefficacious. Not only was there a medicament residue which had to be cleansed from the dactyl but, in addition, since the surface of the dactyl harbored microorganisms, an opportunity was presented for harmful contamination of wounds, open sores and the like. Additionally, transfer to the applicator dactyl of excretions from an infected area occurred. Thus, utilization of this dispensing approach required assiduous digital cleansing both prior to and after dispensing. Further, this approach lacked accurate control of dosage administration.

A further approach used in conjunction with the application of topical medicaments included the use of cotton swabs comprising a wood, paper board or plastic stick with cotton adhered to one or both tips. Medicament was applied to the tip and from the tip to the affected areas. Unfortunately, if the affected areas were difficult to see, e.g. gingiva or other mucosa inside the mouth, it was difficult to accurately dispense the medicament at the affected area. As a result of this shortcoming, many preferred the use of a dactyl.

Another drawback was that the swab tip suffered from an inability to accurately control the quantity of medicament dispensed. The amount of medicament carried by the tip was difficult to control since many medicament bases were not subject to absorption. Usually, an excessive amount of medicament was often carried by the tip. This was either removed prior to dispensing or the affected area was overdosed. Further, precise control over the quantity of medicament dispensed by the tip to the affected area was not available.

In instances where the quantity of medicament on the tip was insufficient, multiple applications, each preferably including the usage of new swabs, was required.

SUMMARY OF THE INVENTION

In compendium, the invention comprises a disposable digital topical medicament applicator which includes a flexible condom-like dactyl cot closed at one end. A medicament carrying dispenser is attached to the closed end of the cot. Preferably, the cot is thin enough to not significantly inhibit tactile sensitivity. As a result, a user is able to obtain accurate dispensing of medicament through tactile positioning and control the quantity dispensed through the use of compressive force.

The dispenser may be formed of a sponge or other absorbent material having the ability to dispense a measured quantity of absorbed material upon the application of compressive force applied by the end of the dactyl. Preferably, the dispenser is conical in configuration having a narrow applicator tip for accurate location and dispensing.

The dispenser may be impregnated with a premeasured dosage of medicament with compression of the end of the dactyl against the affected area resulting in the dispensing of the premeasured dose.

The digital applicator may be packaged in a sealed packet to prevent contamination and/or evaporation of medicament or carrier and to assure stable shelf life. Optionally, the dispenser alone may be covered by a film to prevent evaporation and accidental dispensing of medicament. The packet or film is preferably formed of a liquid and/or gas and liquid impervious material.

From the foregoing summary it will be appreciated that it is an aspect of the present invention to provide a digital applicator of the general character described which is not subject to the disadvantages of the related art aforementioned.

It is a further aspect of the present invention to provide a dactyl applicator of the general character described which facilitates sanitary dispensing of topical medicaments.

A consideration of the present invention is to provide a dactyl applicator of the general character described with a reduced risk of contamination of an affected area of application.

It is a feature of the present invention to provide a digital applicator of the general character described which will allow a person applying a topical medicament to position a medicament dispenser through tactile sensation.

Yet another aspect of the present invention is to provide a dactylic applicator of the general character described which includes an absorbent dispenser impregnated with a premeasured dosage.

A still further consideration of the present invention is to provide a digital applicator of the general character described which reduces wastage of a preparation to be dispensed.

An additional feature of the present invention is to provide a dactylic applicator of the general character described which includes an absorbent dispenser covered by a protective film.

To provide a digital applicator of the general character described which is simple to use is a still further aspect of the present invention.

Another feature of the present invention is to provide a digital applicator of the general character described which is well suited for economical mass production fabrication.

Yet another consideration of the present invention is to provide a dactylic applicator of the general character described which is low in cost and readily disposable.

To provide a dactylic applicator of the general character described encased in a sealed packet for prolonged shelf life and to maintain sanitary or clean applicator surfaces is another consideration of the present invention.

With these other aspects, features and considerations of the present invention in part will be obvious and in part will be pointed out hereinafter.

With these ends in view, the invention finds embodiment in certain combinations of elements, arrangements of parts and series of steps by which the said aspects, features and considerations aforementioned and certain other aspects, features and considerations are hereinafter attained all as fully described with reference to the accompanying drawings and the scope of which is more particularly pointed out and indicated in the appended claims.

BRIEF DESCRIPTION OF THE DRAWINGS

In the accompanying drawings in which is shown one of the possible exemplary embodiments of the invention.

DESCRIPTION OF THE PREFERRED EMBODIMENTS

Figure 1:
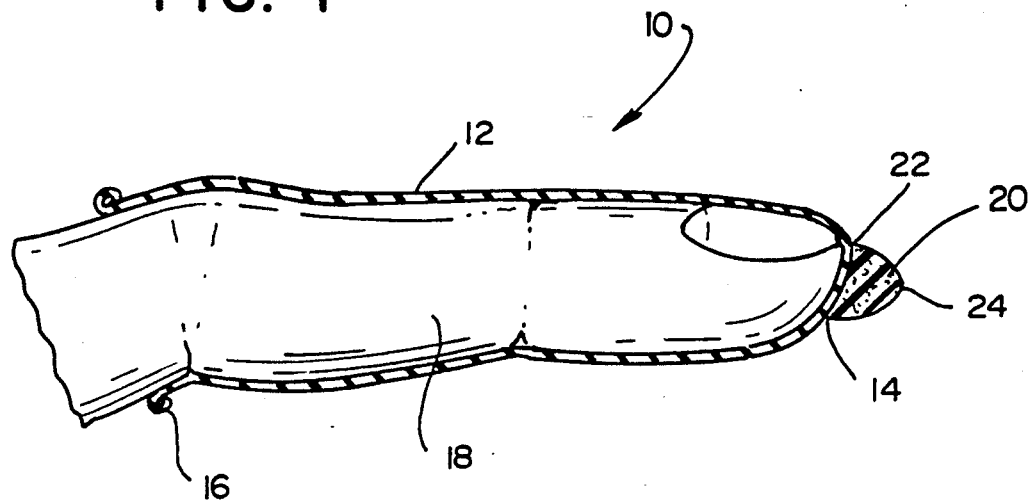
FIG. 1 is a longitudinal sectional view through a digital applicator constructed in accordance with and embodying the present invention as typically mounted on a hand index dactyl and showing an absorbent dispenser secured to the end of the applicator.

Referring now in detail to the drawings, the reference numeral 10 denotes generally a digital applicator constructed in accordance with and embodying the invention. The applicator 10 is formed of a condom-like dactyl cot 12 comprising a thin walled, generally tubular casing having a closed distal end 14. The wall of the cot 12 is coiled about itself to form a toroid 16 at its open end.

The cot is formed of a thin, liquid impervious, material such as latex rubber with the thickness and consistency of a condom so as to provide satisfactory prophylaxis against the transmission of fluid or contaminants between the affected area to be treated and a dactyl 18 such as an index dactyl of the person who is applying the medicament.

It should also be appreciated that the thickness of the cot 12 as illustrated in FIG. 1 is exaggerated in proportion to the dimensions of the cot and the dactyl for the purpose of illustration only. In actuality, the thickness of the cot 12 is significantly less than as proportionately illustrated in FIG. 1. This feature permits substantially encumbered tactile sensation in all areas of the dactyl except, however, at the distal end 14 to which a dispenser 20 is adhered.

The dispenser 20 is formed of an absorbent compressible material such as an open celled sponge and includes a substantially conical configuration having a broad base 22 which is secured to the distal end 14 of the cot 12 and a reduced diameter tip 24. The dispenser is secured to the distal end 14 of the cot 12 by adhesive, heat sealing, ultrasonic welding or other conventional mechanism.

Figure 2:
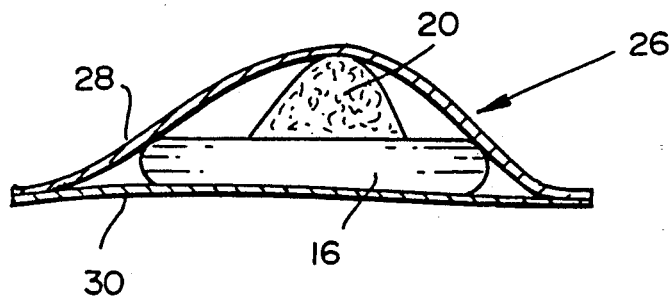
FIG. 2 is a sectional view through a sealed packet containing the digital applicator constructed in accordance with the present invention and showing an applicator casing coiled in a toroid about the dispenser.

Prior to usage, the digital applicator 10 is preferably stored in a sealed packet 26, illustrated in FIG. 2, in a coiled state, that is, with substantially the entire cot casing except the end 14 completely wrapped in the toroid 16 and with the dispenser 20 projecting from the distal end 14 at the center of the toroid.

The packet 26 assures that the digital applicator 10 is clean and free from contamination and maintains sterility if the applicator is presterilized. If the dispenser 12 carries a premeasured dosage of medicament, it is preferable for the packet 26 to be formed of a liquid and/or liquid and gas impervious film. An upper panel or layer 28 and a lower panel or layer 30 are suitably sealed adjacent their common peripheral edges to form the packet 26. Sealing the packet also prevents evaporation of the carrier and/or medicament and also serves to assure a stable shelf life for the applicator.

The use of liquid and/or liquid and gas impervious panels for the packet 26 is equally desirable when the dispenser is not preloaded since it assures that both the dispenser as well as the cot will be maintained relatively clean, if not sterile.

To use the digital applicator 10, the packet 26 is opened, an appropriate dactyl such as the dactyl 18, is selected and the tip of the dactyl is placed against the inner surface of the cot 12 at the distal end 14. Thereafter, the toroid 16 is uncoiled so that the casing of the cot extends toward and covers the base of the dactyl. It should also be noted that the cot 12 is proportioned so that its casing tightly engages the dactyl, thus assuring that there will be no significant loss of tactile sensitivity.

In instances wherein the dispenser is not preloaded, the user then places a desired amount of material to be dispensed on or in the dispenser. If the medicament is in a liquid base, the distal end of the applicator is immersed in the liquid. A predetermined amount of liquid carrying medicament is absorbed into the dispenser in accordance with the absorption characteristics of the dispenser. If the medicament to be dispensed is in a cream or ointment base, a desired amount of medicament is applied to and absorbed into the dispenser by repeated compression and release of the dispenser while in contact with the medicament.

Once loaded, the dactyl is directed to the affected area. In instances wherein the positioning of the dactyl cannot be observed, such as wherein the affected area comprises areas unobservable for self application such as mucosa, tactile sensory perception is utilized to properly position the dispenser by feel. After the affected area has been located, compressive force is exerted toward the affected area with the end of the dactyl pressing against the dispenser. Because the cot is thin the user is able to feel and control other motion. Compression of the dispenser which results in the excretion of the predetermined dosage of medicament on the affected area. Additionally, the dactyl may be moved in a circular, wiping or other motion to utilize the dispenser for the purpose of spreading the dispensed medicament and/or reabsorption of excess medicament. In instances wherein the medicament is preloaded in the dispenser, the user merely dons the applicator on a dactyl by unrolling the toroid and proceeds with dispensing the medicament.

Figure 3:
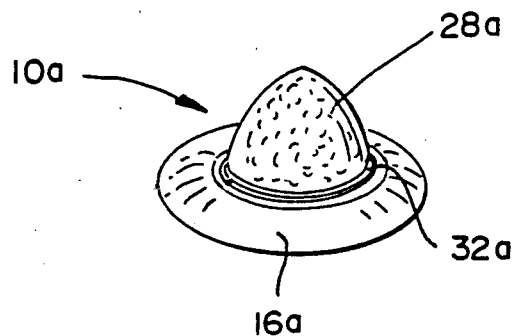
FIG. 3 is a perspective illustration of a further embodiment of the invention illustrating a digital applicator prior to mounting and showing a film covering a dispenser.
Figure 4:
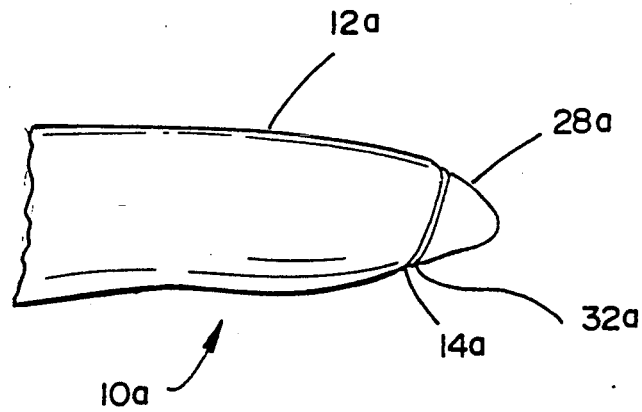
FIG. 4 is a fragmentary elevational view of the digital applicator of FIG. 3, mounted to a dactyl and prior to exposure of the dispenser by removal of the film.

Turning now to FIGS. 3 and 4 wherein an alternate embodiment of the invention is illustrated, like numerals have been utilized to denote like components as described with reference to the previous embodiment, however, bearing the suffix "a". In this embodiment, a digital applicator 10a is formed of a dactyl cot 12a identical in construction to the dactyl cot of the previous embodiment. Attached to a distal end 14a of the cot 12a is a dispenser (not shown) identical in construction to the dispenser previously described and, at the opposite open end of the cot 12a, the casing of the cot is wrapped in a toroid coil 16a.

In accordance with this embodiment of the invention, in lieu of protecting the entire applicator 10 by carrying it within a sealed packet, only the dispenser is covered. A protecting film or layer 28a formed of liquid and/or liquid and gas impervious material is provided to cover the absorbent dispenser. The film 28a is generally conical in shape and includes an annular base flange 32a, having a larger diameter than the base of the dispenser and which is sealed directly against the distal end 14a of the cot 12a. Sealing of the flange 32a may be effected through the use of adhesives, dielectric welding, or other known conventional sealing arrangements.

After removal of the film 28a, the digital applicator 10a is utilized in a manner identical to that previously described with respect to the embodiment of FIGS. 1 and 2.

Thus it will be seen that there is provided a digital applicator which achieves the various aspects, features and considerations and features of the present invention and which is well suited to meet the conditions of practical usage.

It should be appreciated that the digital applicator of the present invention is suited for usage in the dispensing of various products and/or preparations and is not limited in its utility to the dispensing of medicaments. For example, the applicator is well suited for dispensing cosmetics.

As various possible embodiments might be made of the present invention and as various changes might be made in the exemplary embodiments above set forth, it is to be understood that all matter herein described or shown in the accompanying drawings is to be interpreted as illustrative and not in a limiting sense.

Having thus described the invention there is claimed as new and desired to be secured by letters patent claim 1:

1. A digital applicator suitable for topically dispensing a desired amount of a preparation on a selected area, the applicator comprising a dactyl cot, means for dispensing the preparation, and means for fixing the dispensing means to the cot, the cot comprising a tubular casing having an open end and a closed distal end, the dispensing means comprising sponge means for absorbing a quantity of the preparation and for excreting the desired amount of the absorbed preparation on the selected area upon the application of compressive force exerted by a dactyl on which the applicator is mounted, substantially the entire casing except for the distal end being coiled about itself from the open end toward the distal end in a toroid, whereby the applicator may be easily mounted to a dactyl by uncoiling the toroid about the dactyl.

2. A digital applicator suitable for topically dispensing a desired amount of a preparation on a selected area as constructed in accordance with claim 1 wherein the dispensing means is fixed to the distal end of the cot.

3. A digital applicator suitable for topically dispensing a desired amount of a preparation on a selected area as constructed in accordance with claim 1 wherein the sponge is substantially conically shaped, the sponge including an enlarged base and a reduced diameter tip, the means for fixing the dispensing means to the cot fixing the base of the sponge to the cot.

4. A digital applicator suitable for topically dispensing a desired amount of a preparation on a selected area as constructed in accordance with claim 3 wherein the means for fixing comprises an adhesive.

5. A digital applicator suitable for topically dispensing a desired amount of a preparation on a selected area as constructed in accordance with claim 3 wherein the means for fixing comprises a weld.

6. A digital applicator suitable for topically dispensing a desired amount of a preparation on a selected area as constructed in accordance with claim 3 wherein the means for fixing comprises a heat seal.

7. A digital applicator suitable for topically dispensing a desired amount of a preparation on a selected area as constructed in accordance with claim 1 wherein the applicator is carried in a sealed packet prior to uncoiling whereby contamination may be avoided and long shelf life is assured.

8. A digital applicator suitable for topically dispensing a desired amount of a preparation on a selected area as constructed in accordance with claim 1 wherein the preparation comprises a quantity of medicament in a carrier, the quantity of medicament being absorbed in the sponge.

9. A program for using a digital applicator as constructed in accordance with claim 7, the program comprising the steps of:
(a) opening the packet;
(b) placing the end of a dactyl against the end of the cot on a side opposite the side to which the dispensing means is fixed;
(c) covering a portion of the dactyl with the cot by uncoiling the toroid;
(d) locating the selected area; and
(e) dispensing the desired amount of preparation on the selected area by exerting compressive force on the sponge by the tip of the dactyl and between the distal end of the cot and the selected area.

10. A program for using a digital applicator as constructed in accordance with claim 9 further including the step of absorbing a quantity of the preparation in the sponge prior to dispensing the preparation.

11. A program for using a digital applicator in accordance with claim 10 further including the steps of absorbing a quantity of the preparation in the sponge and sealing the digital applicator in the packet prior t opening the packet.

12. A digital applicator suitable for topically dispensing a desired amount of a preparation on a selected area for treatment, the applicator comprising a dactyl cot, means for dispensing the preparation and means for fixing the dispensing means to the cot, the cot comprising a tubular casing having an open end and a closed distal end, the casing being formed of a flexible liquid impermeable film having a wall thickness dimensioned to permit substantially unencumbered tactile sensitivity of a dactyl on which the applicator is mounted over the entire dactyl except for the portion registered with the dispensing means, the dispensing means being fixed to and covering a discrete area of the cot comprising only a minor portion of the cot, the dispensing means comprising sponge means for absorbing a quantity of the preparation and for excreting a desired dosage of the absorbed preparation on the selected area on the application of compressive force exerted by the dactyl.

13. A digital applicator suitable to topically dispensing a desired amount of a preparation on a selected area as constructed in accordance with claim 12 wherein the discrete area comprises the distal end of the casing.

14. A digital applicator suitable for topically dispensing a desired amount of a preparation on a selected area as constructed in accordance with claim 12 wherein the sponge means is substantially conically shaped.

15. A digital applicator suitable for topically dispensing a desired amount of a preparation on a selected area as constructed in accordance with claim 14 further including a conically shaped film of fluid impervious material, the film being removably sealed around and covering the sponge means whereby contamination may be avoided and long shelf life assured.

* * * * *